United States Patent [19]

Sturla

[11] Patent Number: 5,520,200
[45] Date of Patent: May 28, 1996

[54] PROCESS FOR THE NON-LASTING RESHAPING OF KERATINOUS FIBRES

[75] Inventor: Jean-Michel Sturla, Saint-Cloud, France

[73] Assignee: L'Oreal, Paris, France

[21] Appl. No.: 357,373

[22] Filed: Dec. 16, 1994

[30] Foreign Application Priority Data

Dec. 22, 1993 [FR] France .................... 93 15478

[51] Int. Cl.$^6$ ...................................... A45D 7/06
[52] U.S. Cl. ........................... 132/206; 132/211
[58] Field of Search .................... 132/203, 206, 132/210, 211

[56] References Cited

U.S. PATENT DOCUMENTS

| | | | |
|---|---|---|---|
| 3,479,427 | 11/1969 | Lieberman | 132/206 |
| 4,166,473 | 9/1979 | Bauer et al. . | |
| 4,452,261 | 6/1984 | Bresak et al. . | |
| 4,610,261 | 9/1986 | Madrange et al. . | |

FOREIGN PATENT DOCUMENTS

| | | | |
|---|---|---|---|
| 0201622 | 11/1986 | European Pat. Off. . | |
| 2273492 | 1/1976 | France . | |
| 2182205 | 7/1990 | Japan | 132/206 |

*Primary Examiner*—John G. Weiss
*Attorney, Agent, or Firm*—Finnegan, Henderson, Farabow, Garrett & Dunner

[57] ABSTRACT

The invention relates to a treatment process for obtaining a non-permanent reshaping of keratinous fibres, especially the setting of hair, comprising the steps of (i) contacting the fibres, which are maintained under mechanical tension and to which has been applied a composition consisting essentially of at least one polysaccharide and/or polysaccharide derivative, optionally combined with at least one silicone and/or oil, with a gas containing water vapor, the gas having a temperature of at least 75° C., for a time not exceeding 2 minutes to non-permanently reshape the fibres, (ii) cooling the fibres thus contacted, and lastly (iii) removing the mechanical tension which was applied to the fibres, in order to obtain fibres having long-lasting, attractive curls and exceptional cosmetic properties of softness and smoothness.

28 Claims, No Drawings

PROCESS FOR THE NON-LASTING RESHAPING OF KERATINOUS FIBRES

The present invention relates to an improved process for the treatment of keratinous fibres, preferably human keratinous fibres and especially hair, for the purpose of obtaining a non-permanent reshaping and/or restoration of shape of the fibres, especially in the form of a setting. The process of the invention is usable in the field of professional hairdressing, beauty and cosmetic salons, and the like. It relates still more specifically to a process employing water vapour and special treatment substances.

In hairdressing, the term "setting" is known to denote the simple operation which consists of giving the hair an non-permanent and temporary set (generally wavy, such as ringlets, curls and the like) which vanishes instantaneously when the hair is wetted again, especially when the latter is subjected to the action of washing with water or with shampoos. The "setting" process differs from a so-called permanent reshaping operation, during which genuine chemical treatments and/or conversions (reduction/oxidation) have to be carried out on the keratinous fibres, the final shape imposed on the hair becoming no longer sensitive (or remaining only very slightly sensitive) to the above-mentioned external agents.

The most common technique for carrying out setting (or non-permanent reshaping) of hair consists in first placing previously wetted or still wet hair under tension (with traditional supports of the setting curler or roller type, and the like), in then drying the hair thus placed under tension under a salon hair dryer heating to a temperature ranging from 30° C. to 60° C. for a time which can vary from 20 to 60 minutes depending on the bulk of the hair to be dried, in thereafter removing the means for placing under tension used above from the hair thus dried, and lastly in putting the finishing touches to the hair with a comb in order to obtain the hairstyle with the desired final shape. Another, less common, process consists in using the old so-called curling tongs or styling tongs technique (lock of wet hair coiled around a metal core and taken by the latter to more than 100° C. for at least 20 seconds); this latter technique is little used nowadays by professional hairdressers, since it achieves results which are considered on the whole to be unsatisfactory and uneven owing to the fact, in particular, that the hair is subjected to widely differing temperatures according to whether it is in actual contact with the heating core or, on the contrary, some distance away from the latter.

In French Patent Application FR-A-2,273,492 and in U.S. Pat. No. 4,166,473, the entire disclosures, including the drawings, of which are hereby incorporated by reference, it has already been proposed to make use of treatments with superheated steam with the aim, inter alia, of improving the quality and/or the efficiencies of a setting on hair. Although this technique does actually make it possible, compared to the traditional processes, to improve certain features of the set immediately, and especially the setting efficiency (or degree of curling), these improvements nevertheless remain of limited durability (or hold) over time, since they generally disappear within a few days following the treatment. Moreover, independently of the aspect of retention of the degree of curling referred to above, it would naturally be advantageous to be able to have the possibility of curly hair displaying an initial degree of curling (i.e. immediately after setting treatment) which is still further improved compared to what is known at the present time, with or without steam treatment. Lastly, the above steam process has another major drawback, namely that of finally resulting in fibres which seem rough to the touch, which is undesirable from a cosmetic standpoint.

The aim of the present invention is, in particular, to solve the above problems.

More specifically, the object of the present invention is to provide a new treatment process suitable for the non-permanent reshaping of keratinous fibres, preferably human keratinous fibres, and especially hair, which makes it possible to obtain curling of high quality.

Another object of the present invention is to provide a process as above which enables, in addition, this curling to be preserved on a long-lasting basis (retention).

Yet another object of the invention is to provide a process as above that makes it possible to obtain keratinous fibres which are reshaped non-permanently while displaying exceptional cosmetic properties of softness and smoothness.

Following a considerable amount of research, it has now been found by the inventor, most unexpectedly and surprisingly, that these and other objects of the invention may be achieved by using water vapour under certain special conditions on keratinous fibres, preferably human keratinous fibres, and especially hair, previously treated with polysaccharides and/or polysaccharide derivatives, optionally in combination with silicones and/or oils. This discovery underlies the present invention.

The present invention thus provides a new process suitable for the non-permanent reshaping and/or restoration of shape of keratinous fibres, preferably human keratinous fibres, and especially hair. This process comprises the steps of (a) contacting said fibres, said fibres being maintained under mechanical tension (rollers, curlers or the like) and having had applied thereto a composition containing at least one polysaccharide and/or polysaccharide derivative, with a gas containing water vapour, said gas having a temperature of at least 75° C., for a time not exceeding 2 minutes to non-permanently reshape said fibres, (b) cooling said fibres after said contacting step, and (c) removing the mechanical tension which was applied to said fibres.

Although the description which follows chiefly centres on the special case of the treatment of hair, it may be noted here that the process according to the invention is preferably applicable to any human keratinous substance in general, in particular eyelashes, moustaches, and hairs generally, as well as to non-human keratinous fibres, for example, the hair of show dogs.

The gas used in the process of the present invention preferably contains at least 1% by volume of water vapour. In addition to water vapour, the carrier gas (or gaseous vehicle) can contain solvent vapour, as well as gases such as oxygen or nitrogen, mixtures of gases such as air or alternatively other vapourizable compounds.

As solvents which can advantageously be used for the production of vapour (water/solvent mixtures), use may be made of cosmetically acceptable organic solvents such as, for example, alcohols such as ethanol, isopropanol, benzyl alcohol and phenylethyl alcohol, or glycols or glycol ethers such as, for example, ethylene glycol and its monomethyl, monoethyl and monobutyl ethers, propylene glycol, butylene glycol, dipropylene glycol and also alkyl ethers such as diethylene glycol monobutyl ether.

According to the present invention, the gas preferably consists either exclusively or chiefly of water vapour, or of a mixture of water and air. The temperature of the gas is preferably above or equal to 85° C., and more preferably ranges from 85° C. to 150° C., approximately. Still more preferably, the temperature ranges from 75° C. to less than 105° C. The temperature can also range from 75° C. to less than 100° C. The time of contact between the hot treatment gas and the fibre should be brief, and should preferably not exceed 2 minutes. Preferably, the gas is brought into contact with the fibre for a time ranging from 0.01 second to 30 seconds, more preferably from 1 to 20 seconds, and still more preferably from 1 to 10 seconds. Naturally, the application of the gas may be repeated several times on the same fibre, each operation being carried out on the basis of a time as stated above.

A preferred embodiment of the process according to the invention consists in first applying to the hair a composition consisting partly or completely of polysaccharides and/or polysaccharide derivatives, it being possible for this application to be carried out before, during or after the customary operation of placing the locks of hair under tension in a shape corresponding to the final shape desired for these latter, e.g., ringlets. This operation may be carried out by any suitable means known per se, in particular a mechanical means, for maintaining hair wider tension, such as, for example, tubular bodies, rollers, curlers and the like. The locks thus impregnated with polysaccharides (or with polysaccharide derivatives) are then subjected briefly to the action of water vapour according to the conditions mentioned above, and are then cooled, preferably rapidly, for example, by passing a stream of air at room temperature over or through them and/or by drawing a stream of ambient air through the coiled locks. Finally, the mechanical means which maintained the locks under tension and in the desired shape throughout the whole treatment is removed from the hair, resulting in locks or a head of hair displaying, for example, attractive, even and soft ringlets.

In another embodiment of the present invention, the hair is put under mechanical tension as described above and a composition consisting partly or completely of polysaccharides and/or polysaccharide derivatives is applied to the hair simultaneously with a gas containing water vapour, as described above. The locks of hair thus treated are then cooled, preferably rapidly, by a method as set forth above, and finally, the mechanical means which maintained the locks under tension and in the desired shape throughout the whole treatment is removed from the hair, resulting here also in locks or a head of hair displaying, for example, attractive, even and soft ringlets.

The production of a hot gas comprising water vapour can be done using any apparatus known per se and designed for this purpose. However, according to the invention, it is preferable to use an apparatus such as the one described in French Patent Application FR-A-2,273,492 or in U.S. Pat. No. 4,166,473, the disclosures of which were incorporated by reference above, or any other equivalent apparatus, which is, in effect, particularly suitable in the present case as it provides steady and homogeneous selective treatment of the fibres without risk of overheating and with integrated post-treatment cooling.

According to the present invention, it is possible to use any polysaccharide or any polysaccharide derivative known per se, including a homopolysaccharide or heteropolysaccharide, of animal, vegetable, microbial, bacterial or synthetic origin.

Generally speaking, the polysaccharides and their derivatives which are usable in the context of the present invention are those which are described in the Kirk-Othmer Encyclopedia of Chemical Technology, 3rd Edition, vol. 3, pp. 896–900, and vol. 15, pp 439–458" (1982), in "Polymers in Nature", E. A. MacGregor and C. T. Greenwood, Eds., pp 240–328 (1980), and in "Industrial Gums—Polysaccharides and their Derivatives," Roy L. Whistler, Ed., 2nd Edition, the disclosures of these three works being hereby fully incorporated by reference.

According to the present invention, it is possible either to use one polysaccharide and/or one of its derivatives on its/their own or to employ several different polysaccharides and/or polysaccharide derivatives.

As examples of polysaccharides or polysaccharide derivatives suitable for carrying out the process according to the invention, there may be mentioned, in particular, glucans, starches, modified or otherwise (such as those taken, for example, from cereals such as wheat, maize or rice, legumes such as peas, tubers such as potatoes or manioc), amylose, amylopectin, glycogen, dextrans, β-glucans, celluloses and their derivatives (methylcelluloses, hydroxyalkylcelluloses, ethylhydroxyethylcelluloses, carboxymethylcelluloses), fructosans, inulin, levan, mannans, xylans, lignins, arabans, galactans, galacturonans, chitin, glucoronoxylans, arabinoxylans, xyloglucans, glactomannans, glucomannans, pectic acids and pectins, alginic acid and alginates, arabinogalactans, carrageenans, agars, glycosaminoglucans, gum arabics, gum tragacanths, ghatti gums, karaya gums, carob gums, guar gums and xanthan gums.

According to an especially preferred embodiment of the process according to the invention, the polysaccharides used are chosen from starches and celluloses, optionally modified, as well as their derivatives.

Modified starches or celluloses are understood to mean starches or celluloses which have been subjected to traditional chemical operations such as pregelatinization, hydrolysis (maltodextrin, glucose syrup), roasting (dextrin, yellow dextrin, white dextrin), oxidation, crosslinking, esterification, etherification, grafting or quaternization, with the object either of modifying some of their physical properties or of introducing new functionalities into the molecule (modification of the chemical properties), such as, for example, anionic groups (phosphates, sulphates, sulphonates, carboxylates or dicarboxylates, such as acetates, adipates, acrylates, crotonates and octenylsuccinates, and the like), cationic groups (quaternary ammonium) or neutral groups (acetyl and hydroxyalkyl, for example).

According to the present invention, the polysaccharides may be employed on their own, but it is preferable to use compositions containing such polysaccharides in a cosmetically acceptable vehicle. They can thus be either solubilized or made into dispersions or (micro)emulsions in aqueous media or organic media or alternatively aqueous-organic media. As suitable organic solvents, monohydric alcohols or polyols (ethanol, isopropanol, glycerol, benzyl alcohol, glycols), acetone, polyol ethers, hydrocarbons, esters, dimethoxymethane or alternatively volatile silicones may be mentioned in particular.

According to another embodiment of the present invention, the above compositions contain, in addition, at least one silicone (silicone oil, resin or gum, or alternatively volatile silicone) and/or at least one oil (mineral, animal, vegetable or synthetic), for example a polydimethylsiloxane, petroleum jelly or an isoparaffin. The silicone may be present in an amount preferably ranging from 0.01 to 50%, more preferably 0.1 to 10%, by weight relative to the whole composition. The oil may be present in an amount preferably ranging from 0.01 to 50%, more preferably 0.1 to 10%, by weight relative to the whole composition. The addition of a silicone and/or an oil makes it possible to obtain hair which, at the end of the treatment, has improved cosmetic properties, especially softness and smoothness.

The contents of polysaccharide(s) (or of polysaccharide derivatives) in the compositions can vary within very wide limits, and can range, for example, from 0.01% to 50%, and preferably from 0.1 to 30%, by weight relative to the whole of the composition.

The compositions can take any form customarily used in the field of hair-care compositions for topical use, such as, for example, more or less thickened or gelled liquid, cream, mousse, lotion, gel, paste, emulsion, aerosol or any other suitable form.

The polysaccharide-based compositions can thus, and generally speaking, contain all the various traditional additives which are used in the field of the preparation of hair-care compositions for topical use, and can be chosen, for example, from UV screening agents, thickening agents, penetrating agents, antioxidants, sequestering agents, opacifying agents, buffers, surfactants chosen from nonionic surfactants such as alkyl polyglycosides, cationic surfactants, anionic surfactants and amphoteric surfactants, solubilising agents, emollients, colorants, perfumes and preservatives.

The polysaccharide-based compositions used in the context of the present invention, which are hence intended for application to hair, preferably have a pH ranging from 3 to 11. If necessary, this pH may be adjusted to the desired value by adding, as appropriate, either standard alkalinizing agents or standard acidifying agents which are known to be cosmetically acceptable.

Specific, but in no way limiting, examples illustrating the invention will now be given. For the purposes of a significant comparison, the same initial locks of hair (before treatment) were used for all the examples.

EXAMPLE 1

A polysaccharide-based composition 1 having the following features (% by weight) was used:

| | |
|---|---|
| Modified starch marketed by NATIONAL STARCH & CHEMICAL under the brand name PURITY GUM 59 (100% of AS) | 3% |
| Distilled water qs | 100% |

This composition was packaged in a pump bottle dispensing 0.15 ml doses per spraying.

4 sprayings of the above composition were applied to a lock of natural hair and the lock thus treated was then coiled on a curler 20 mm in diameter. The coiled lock was then treated for 5 seconds by means of a jet of gas essentially containing only water vapour and the temperature of which was 85° C. The lock was then rapidly cooled by means of a stream of ambient air and, lastly, was uncoiled from the curler.

To quantify the efficacy of the process according to the invention, the initial length $L_0$ (in cm) of the lock of hair was first measured before the vapour treatment (length measured between the roots and the ends on the vertically suspended lock); in the same way, the length $L_1$ of this same lock was measured immediately after the treatment had ended; and lastly the length $L_2$ of this lock was measured 48 hours after the treatment.

The setting, or curling, efficiency, p, (in %) is defined by the ratio:

$$p = \frac{L_0 - L_1}{L_0} \times 100$$

The curl retention, r, (in %) of the set is defined by the ratio:

$$r = \frac{L_0 - L_2}{L_0} \times 100$$

The higher the value of one and/or the other (and preferably of both at once) of these two ratios, the better the set will be.

The results obtained were as follows:

$L_0$=24 cm; $L_1$=16 cm (p=33%); $L_2$=17 cm (r=29%)

By way of comparison, the results obtained in the case of a vapour treatment conducted on locks not previously treated with polysaccharides were as follows:
$L_0$=24 cm; $L_1$=18 cm (p=25%); $L_2$=23 (r=4%)

EXAMPLE 2

The procedure was like that used in Example 1, except that a polysaccharide-based composition 2 having the following features (% by weight) was used:

| | |
|---|---|
| Pregelatinized and quaternized starch (potato flour) marketed by AVEBE wider the brand name SOLVITOSE N (100% of AS) | 2% |
| Distilled water qs | 100% |

The results obtained were comparable to those of Example 1.

EXAMPLE 3

The procedure was like that used in Example 1, except that a polysaccharide-based composition 3 having the following characteristics (% by weight) was used:

| | |
|---|---|
| Starch (potato flour) phosphate marketed by AVEBE wider the brand name RETABOND AP (100% of AS) | 3% |
| Distilled water qs | 100% |

The results obtained were comparable to those of Example 1.

EXAMPLE 4

The procedure was like that used in Example 1, except that a polysaccharide-based composition 4 having the following features (% by weight) was used:

| | |
|---|---|
| Sodium carboxymethylcellulose marketed by AQUALON wider the brand name AMERGUM 1221 (100% of AS) | 3% |
| Distilled water qs | 100% |

The results obtained were comparable to those of Example 1.

All the above results show clearly the improvements brought about with respect to efficiency and retention for the sets obtained by the process according to the invention. Moreover, all the locks of hair pretreated with a polysaccharide in combination with a silicone and/or an oil afforded exceptional softness and smoothness to the touch.

What is claimed is:

1. A process for non-permanent reshaping of human keratinous fibres, comprising the steps of:
    (a) contacting said fibres, said fibres being maintained under mechanical tension and having had applied thereto a composition consisting essentially of at least one polysaccharide and/or polysaccharide derivative, with a gas containing water vapour, said gas having a temperature of at least 75° C., for a time not exceeding 2 minutes to non-permanently reshape said fibres;
    (b) cooling said fibres after said contacting step; and
    (c) removing the mechanical tension which was applied to said fibres.
2. A process according to claim 1, wherein said gas has a temperature above or equal to 85° C.
3. A process according to claim 2, wherein said temperature ranges from 85° C. to 150° C.
4. A process according to claim 1, wherein said gas has a temperature which ranges from 75° C. to less than 105° C.
5. A process according to claim 1, wherein said gas is brought into contact with the fibre to be reshaped for a time ranging from 0.01 second to 2 minutes.
6. A process according to claim 5, wherein said time ranges from 0.01 second to 30 seconds.
7. A process according to claim 6, wherein said time ranges from 1 second to 20 seconds.
8. A process according to claim 7, wherein said time ranges from 1 second to 10 seconds.
9. A process according to claim 1, wherein the application of the gas is repeated several times on the fibres.
10. A process according to claim 1, wherein said gas contains only water vapour.
11. A process according to claim 1, wherein said gas contains water vapour and at least one other compound in gas or vapour form.
12. A process according to claim 11, wherein said gas contains water vapour and air.
13. A process according to claim 1, wherein the polysaccharide is selected from starches and celluloses, optionally modified, as well their derivatives.
14. A process according to claim 1, wherein at least one silicone and/or oil is applied in addition to the keratinous fibres before said fibres are brought into contact with the gas.
15. A process according to claim 1, wherein the polysaccharide and/or polysaccharide derivative composition further contains at least one additive selected from UV screening agents, thickening agents, penetrating agents, antioxidants, sequestering agents, opacifying agents, buffers, nonionic surfactants, cationic surfactants, anionic surfactants, amphoteric surfactants, solubilising agents, emollients, colorants, perfumes and preservatives.
16. A process according to claim 1, wherein the keratinous fibres are hair.
17. A process for non-permanent reshaping of keratinous fibres, comprising the step of contacting said fibres, said fibres being maintained under mechanical tension and having had applied thereto a composition consisting essentially of at least one polysaccharide and/or polysaccharide derivative, with a gas containing water vapour, said gas having a temperature of at least 75° C., for a time not exceeding 2 minutes to non-permanently reshape said fibres.
18. A process according to claim 17, wherein the keratinous fibres are human keratinous fibres.
19. A process for non-permanent reshaping of keratinous fibres, comprising the steps of:
    (a) contacting said fibres, said fibres being maintained under mechanical tension, with a composition consisting essentially of at least one polysaccharide and/or polysaccharide derivative and with a gas containing water vapour, said gas having a temperature of at least 75° C., for a time not exceeding 2 minutes to non-permanently reshape said fibres;
    (b) cooling said fibres after said contacting step; and
    (c) removing the mechanical tension which was applied to said fibres.
20. A process according to claim 19, wherein the keratinous fibres are human keratinous fibres.
21. A process for non-permanent reshaping of keratinous fibres, comprising the steps of:
    (a) contacting said fibres, said fibres being maintained under mechanical tension and having had applied thereto a composition consisting essentially of at least one polysaccharide and/or polysaccharide derivative, with a gas containing water vapour, said gas having a temperature of at least 75° C., for a time sufficient to non-permanently reshape said fibres into long-lasting curls;
    (b) cooling said fibres after said contacting step; and
    (c) removing the mechanical tension which was applied to said fibres.
22. A process according to claim 21, wherein the keratinous fibres are human keratinous fibres.
23. A process according to claim 21, wherein the temperature of said gas ranges from 75° C. to less than 105° C.
24. A process for non-permanent reshaping of keratinous fibres, comprising the steps of:
    (a) contacting said fibres, said fibres being maintained under mechanical tension and having had applied thereto a composition consisting essentially of at least one polysaccharide and/or polysaccharide derivative, with a gas containing water vapour for a time not exceeding 2 minutes, said gas having a temperature sufficient to non-permanently reshape said fibres into long-lasting curls;
    (b) cooling said fibres after said contacting step; and
    (c) removing the mechanical tension which was applied to said fibres.
25. A process according to claim 24, wherein keratinous fibres are human keratinous fibres.
26. A process according to claim 24, wherein said gas is brought into contact with the fibre to be reshaped for a time ranging from 1 to 10 seconds.
27. A process for non-permanent reshaping of keratinous fibres, comprising the steps of:
    (a) contacting said fibres, said fibres being maintained under mechanical tension and having had applied thereto a composition consisting essentially of at least one polysaccharide and/or polysaccharide derivative, with a gas containing water vapour, said gas having a temperature and said contact time being sufficient to non-permanently reshape said fibres into long-lasting curls;
    (b) cooling said fibres after said contacting step; and
    (c) removing the mechanical tension which was applied to said fibres.
28. A process according to claim 27, wherein the keratinous fibres are human keratinous fibres.

* * * * *